United States Patent [19]
Heckman

[11] Patent Number: 5,591,901
[45] Date of Patent: Jan. 7, 1997

[54] FLUID SENSOR

[75] Inventor: James R. Heckman, Palm Harbor, Fla.

[73] Assignee: Ryland Engineering Corporation, Palm Harbor, Fla.

[21] Appl. No.: 226,958

[22] Filed: Apr. 13, 1994

[51] Int. Cl.$^6$ .......................... G01N 33/18; G01N 33/26; G01N 37/00
[52] U.S. Cl. ........................................ 73/61.43; 73/61.61
[58] Field of Search ............................ 73/61.43, 61.61; 324/453, 698, 655

[56] References Cited

U.S. PATENT DOCUMENTS

| | | | |
|---|---|---|---|
| 3,546,926 | 12/1970 | Dunavent, Jr. et al. | 73/61.43 |
| 3,774,185 | 11/1973 | Parth | 73/61.43 |
| 4,011,746 | 3/1977 | Weitz, Jr. et al. . | |
| 4,082,997 | 4/1978 | Ohtsu et al. | 324/698 |
| 4,102,177 | 7/1978 | Okada et al. . | |
| 4,147,051 | 4/1979 | Griffiths et al. . | |
| 4,251,809 | 2/1981 | Cheney | 73/61.43 |
| 4,260,950 | 4/1981 | Hadden et al. | 324/425 |
| 4,266,195 | 5/1981 | Keefner et al. | 324/439 |
| 4,429,270 | 1/1984 | Davies et al. . | |
| 4,470,300 | 9/1984 | Kobayashi | 73/61.43 |
| 4,544,880 | 10/1985 | Nagy et al. . | |
| 4,721,950 | 1/1988 | Andrejasich et al. | 73/61.43 |
| 4,751,476 | 6/1988 | Meijer . | |
| 4,811,592 | 3/1989 | Miura et al. . | |
| 4,873,648 | 10/1989 | Mouser et al. | 73/61.43 |
| 4,890,480 | 1/1990 | Young . | |
| 4,916,940 | 4/1990 | Mougne | 73/61.43 |
| 4,956,793 | 9/1990 | Bonne et al. . | |
| 4,961,345 | 10/1990 | Tsuruoka et al. . | |
| 5,025,656 | 6/1991 | Wright . | |
| 5,028,144 | 7/1991 | Klein | 73/61.43 |
| 5,028,394 | 7/1991 | Lowell, Jr. et al. . | |
| 5,033,289 | 7/1991 | Cox | 73/61.43 |
| 5,033,293 | 7/1991 | Honma et al. | 73/61.43 |
| 5,034,192 | 7/1991 | Wrighton et al. . | |
| 5,301,542 | 4/1994 | Meitzler et al. | 73/61.43 |
| 5,416,425 | 5/1995 | Mouaici | 73/61.43 |

FOREIGN PATENT DOCUMENTS

| | | | |
|---|---|---|---|
| 206466 | 12/1954 | Australia | 73/61.43 |
| 2837920 | 3/1980 | Germany | 73/61.43 |

OTHER PUBLICATIONS

Bock et al., "Detection of Oil in Sewers", IEEE Transactions on Geoscience Electronics, vol. GE-10, No. 2, Apr. 1972, pp. 119-126.

Primary Examiner—Hezron E. Williams
Assistant Examiner—Daniel S. Larkin
Attorney, Agent, or Firm—Allen, Dyer, Doppelt, Franjola & Milbrath, P.A.

[57] ABSTRACT

A sensor can detect the difference in potential between itself and the fluid into which it is immersed, a signal generated by the probe representing this difference in potential. This signal is used to activate an oscillator circuit. By varying the conditions at which current in the oscillator circuit begins to oscillate, various liquids can be detected and identified.

20 Claims, 5 Drawing Sheets

FLUID SENSOR

BACKGROUND OF THE INVENTION

The prior art lacks an extremely reliable type of sensor or detection device that can distinguish between oil and water. Furthermore, it is important that such a device is able to detect the difference between the type of fluid, for example, such as the various grades of refined fuel/oil and water. Such a device, when incorporated into a pump control system, should be able to carry out each of the following functions:
1. Cause a pump to be turned on or off when water or oil/fuel is detected in a storage system;
2. Give an indication that oil or water has been sensed;
3. Provide a means to detect the presence and amount of emulsion in unctuous fluids.
4. Sense a particular grade of oil and cause activation of an alarm, pump, or indicator light.
To date, no such device has been available.

SUMMARY OF THE INVENTION

The invention is generally described as a detection device which may comprise one or more sensors which are preferably in operable communication with AC or DC pumps, alarm circuits, or control apparatus.

The sensor can detect the difference in potential between itself and the fluid into which it is partially immersed, and it can generate an output signal representing this difference in potential. This signal is used to activate an oscillator circuit. By varying the conditions, or parameters, at which current flowing through the oscillator circuit begins to oscillate, various liquids can be identified. By the use of multiple sensors, each set to determine a different material, an effective method results for detecting the presence of an excess of one fluid in another fluid, or in appropriately selected areas of a vessel or tank. The sensor is in communication with electronic circuitry, such as a conventional microprocessor, capable of automatically activating a pump or alarm when certain fluids are detected or reach a dangerously abnormal level.

OBJECTS OF THE INVENTION

It is an object of the invention to have a sensor which can distinguish between various types of fluids.

It is a further object of the invention to have a detecting device which can automatically activate pump control circuits.

It is a further object of the invention to provide an electric sump pumping assembly with an alarm and maintenance feature which can be easily monitored.

It is a further object of the invention to provide a highly reliable bilge alarm system that can be used on any type of vessel to alert a crew of a flood level condition or fuel spill.

These and other objects are achieved by a probe capable of detecting an electrical potential between itself and the fluid, the probe having an output circuit therein producing an output signal when the electrical potential reaches a predetermined value.

DETAILED DESCRIPTION OF THE INVENTION

It has been found that an electrical potential between a fluid and a probe immersed therein may cause oscillation of current in an oscillator circuit, such oscillation being translated into an output signal indicating presence of a fluid and/or causing activation of external devices. Such electrical potential, hereinafter referred to as a "field effect", is caused by the differential charge between the probe and the positively charged molecules comprising the detected fluid into which the probe has been partially immersed. This field effect provides the work necessary to liberate electrons within the probe or within material encasing it, and the liberated electrons comprise current flow which is routed to the oscillator circuit, thereby causing oscillation upon the occurrence of certain conditions, resulting in transmission of an output signal to initiate performance of a given task.

STRUCTURE OF THE PREFERRED EMBODIMENT

Figure 1:
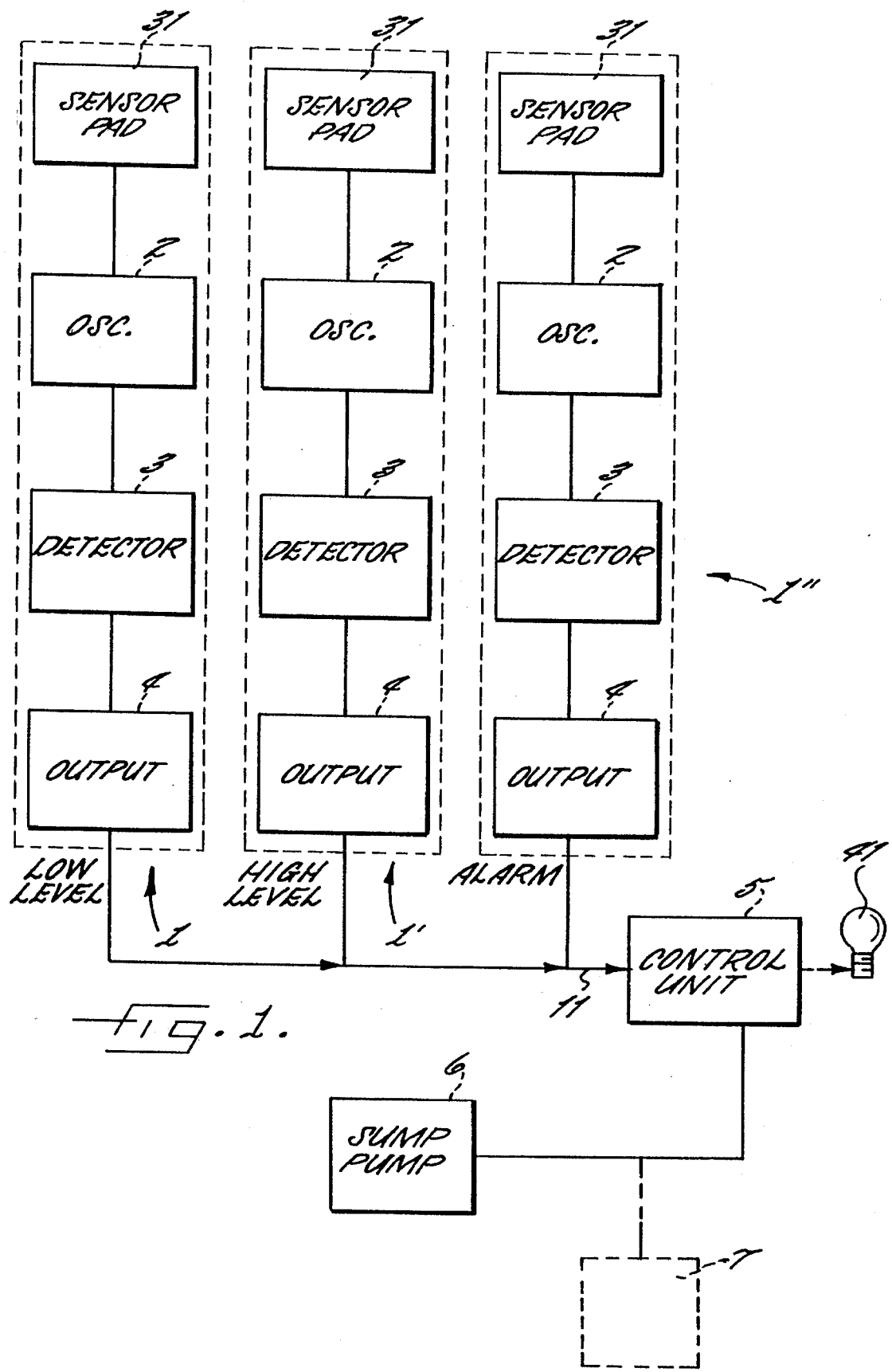
FIG. 1 is a block diagram showing a detection device constructed in accordance with a preferred embodiment of the present invention.

FIG. 1 shows a block diagram of an apparatus for detecting a given fluid, such as water, and which can cause activation of external device, such as an alarm or sump pump upon detection. The device chiefly comprises one or more probes, such as at 1, 1', and 1". A sensor pad 31 detects a given fluid in response to the field effect between the sensor pad 31 and fluid into which a probe 1 containing sensor pad 31 is immersed (see FIG. 3). The term "immersed" is used herein to refer to either partial or total immersion of the pad 31 into the fluid. The probe 1 may be immersed into a naturally occurring body of fluid, or it may be immersed into a fluid 70 contained by an enclosure 72, such as a tank.

When the field effect is generated and when fluid is present which corresponds to a resistor 16 in an oscillator circuit 2 (FIG. 4), as will be described in greater detail herein, current within the oscillator circuit 2 begins to oscillate. These oscillations take the form of alternating current (AC) signals which are detected by a detector circuit 3 interfacing with the oscillator circuit 2. The detector circuit 3 modifies the AC signal and then sends it to an interfacing amplifier circuit 10 (FIG. 4), from which it proceeds to an output circuit 4, which converts the modified, amplified AC signal into a logic signal. That logic signal is sent via leads, such as at 11, to a control unit 5. The control unit 5 then, depending upon the state of the logic signal, can indicate the presence of a liquid, the liquid level in an enclosure once the depth of insertion of the pad 31 into the enclosure is known, turn on an alarm 7, or activate another external device, such as a sump pump 6, which would start removing the detected liquid. In the latter arrangement, control unit 5 could also actuate monitoring means, such as a 2-digit light-emitting diode (LCD) counter, each time sump pump 6 is activated, thereby enabling a user to monitor the number of cycles performed by sump pump 6. In the absence of control unit 5, the function of the logic signal from output circuit 4 is limited to activation of an LED light 41.

Having described the invention in general terms, the invention will be described in more detail with attention being directed to FIGS. 2–4.

Figure 2:
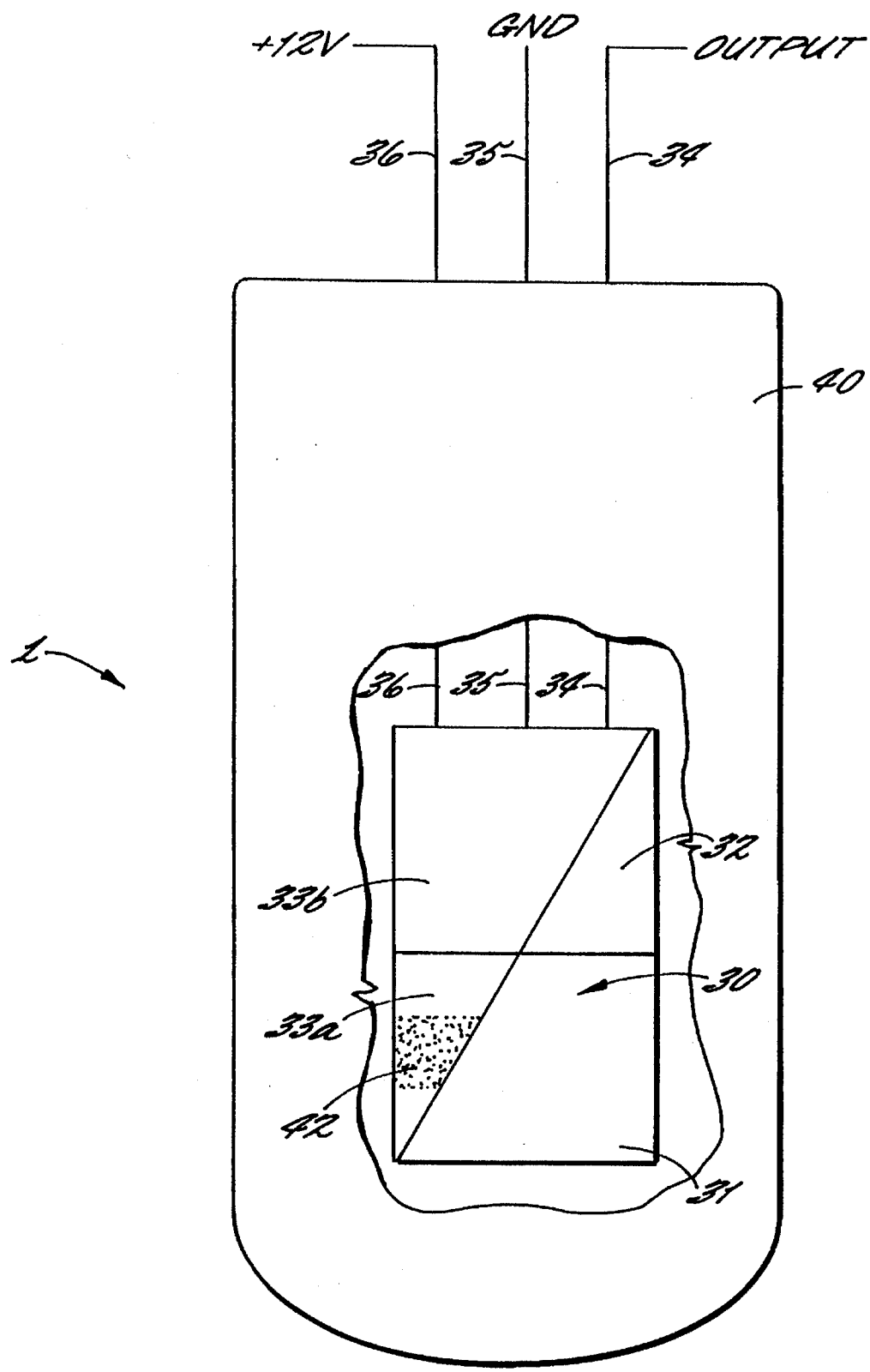
FIG. 2 is a partial cutaway view of the probe of the detecting device shown in FIG. 1.
Figure 3:
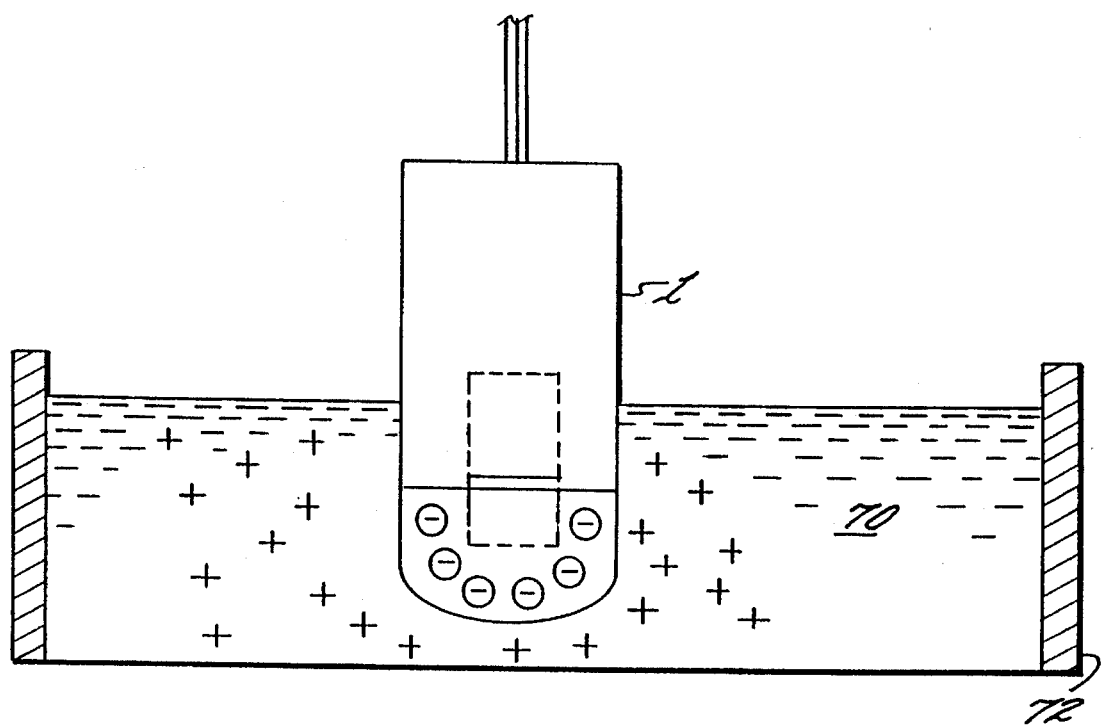
FIG. 3 is a view of the probe of FIG. 1 submerged in a liquid to be analyzed.

FIG. 2 shows a probe 1 used in the present invention. The probe 1 comprises a printed circuit (PC) board 30 encapsulated by a potting material 33a, 33b, which is preferably an epoxy resin. Surrounding the potting material 33a, 33b is an inert and non-conductive shell 40. The PC board 30 has a pad area 31, which is constructed of a metallic conductive material, and a circuit area 32. The circuit mounted to the circuit area 32 is shown in FIG. 4 and will be described in detail below. Finally, extending from the PC board 30 are an output line 34, a +12 Volt DC power supply line 36, and a ground line 35.

In the pad area 31 of the PC board 30, an additive 42 comprised of atoms characterized by a low ionization potential, such as graphite or powdered silver, is added to the potting material 33a. The enhanced potting material increases the effective area of the pad 31 by increasing the sensitivity of the probe to positively charged molecules. While additive-to-potting ratios on the order of 0.5–1.0 grams/ounce are acceptable, sensitivity of the probe is reduced by 60% when going from 1.0 grams/ounce to 0.5 grams/ounce.

The sensitivity of the pad is determined not only by the amount of additive in the potting mixture but also by the dimensions of the pad itself. The Sensitivity factor ($S_f$) of the probe is determined by the following formula:

$$S_f = (100/A)*(b/c)$$

Wherein:
$S_f$=sensitivity factor
A=Pad area (sq. cm)
b=quantity of resin (mg)
c=reciprocal of concentration of resin to additive ratio (e.g., 4:1=0.250)

The sensitivity of the pad determines the depth of its immersion, into the fluid being analyzed, at which it can detect a particular fluid. For example, a probe with a high sensitivity would only need to be inserted about ⅜" into the fluid, while a probe with a low sensitivity would have to be inserted much deeper, for example ¾".

Once the pad area 31 has been coated with the epoxy resin material 33a, 33b, the fluid need not be in direct contact with the sensor pad 31. Therefore, the sensor pad 31 can be enclosed in a protective shield 40 made of inert and non-conductive material such as poly-vinyl chloride (PVC), which is an excellent material for this application because not only is it chemically inert but it is also a non-conductive material through which the field effect is still felt, due to the enhanced sensitivity of the pad stemming from the additive-laden potting material 33a, 33b. This PVC shell 40 strictly protects the probe from contaminates that may be found in the fluids.

The principal behind the operation of the probe 1 is the fact that unctuous fluids, i.e., those containing fats or oils, contain hydrocarbon molecules, which are known to generally have a positive charge. If the charge within the fluid is more positive than the charged probe 1, the sensor pad 31 will detect that difference and generate an output. Similarly, if the fluid is more negatively (e.g., less positively) charged than the sensor, an output is likewise generated.

Figure 4:
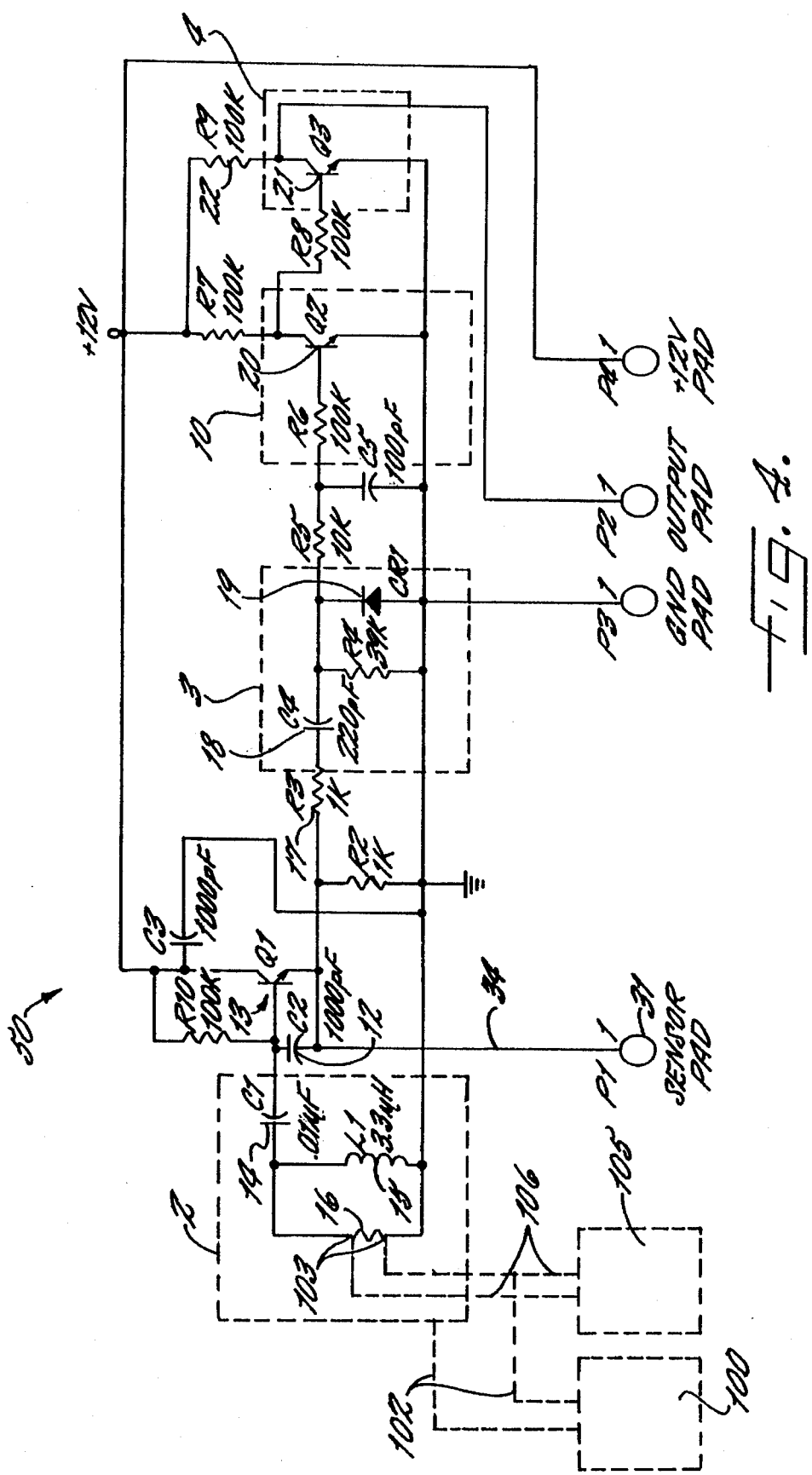
FIG. 4 is a schematic diagram of the circuit used in the detecting device shown in FIG. 1.

FIG. 4 shows the circuit 50 controlling the detecting device constructed in accordance with the preferred embodiment. When the field effect occurs between the probe 1 and the fluid into which it is immersed, it causes the easily-liberated electrons in the potting material additive 42 (FIG. 2) to flow as current through output 34 and into oscillator circuit 2. If the resistance in a resistor 16 of that circuit corresponds to a particular fluid present in the fluid being detected by probe 1 (hereinafter referred to as "oscillation conditions"), as will be explained in greater detail herein, the current flowing through oscillator circuit 2 will begin to oscillate.

The oscillator circuit 2 is primarily comprised of a first capacitor 14 and an inductor 15 connected in series to the pad 31, and of a resistor 16 connected in parallel to the inductor 15. The component values of the oscillator circuit 2, i.e., the resistance of resistor 16, the capacitance of capacitor 14, and the inductance and "Q-value" (an indicator of the capacity of an inductor to generate an electrical field thereabout) of inductor 15, preferably allow the oscillator circuit 2 to sustain a frequency of approximately 10 Mega-Hertz, although oscillation at different frequencies is contemplated by the present invention.

The current flowing into oscillator circuit 2 causes a change in voltage across a second capacitor 12, which is felt by the transistor 13. Transistor 13 is biased to be activated responsive to a slight change in the voltage across second capacitor 12. If oscillation conditions are present, transistor 13 will send a signal to the remainder of circuit 50 responsive to oscillating current. That current oscillates by first flowing through inductor 15, then onto a plate of capacitor 14, thereby building charge thereon. As that charge builds, the electric field around inductor 15 collapses, which, in turn, causes the capacitor 14 to discharge. The charging and discharging of capacitor 14 is cyclic; consequently, the corresponding voltage change across capacitor 12 is likewise cyclic. Responsive to this cyclic change of voltage, transistor 13 periodically transmits current, now in the form of an AC signal, to the remainder of circuit 50.

The AC signal from transistor 13 is felt across a resistor 17 interfacing with a detector circuit 3, into which the AC signal enters. The detector circuit 3, by use of capacitor 18 and diode 19, removes the negative portion of the AC signal. The remaining positive portion of the AC signal causes an amplifier circuit 10 to drive an output circuit 4 to produce a logic high output. Capacitor 18 also prevents any DC potential from transistor 13 from reaching a transistor 20 of amplifier circuit 10.

The output circuit 4 sends a signal sufficient to cause transistor 20 to turn on and gate the signal to output transistor 21. When transistor 21 is turned on, a voltage drop across resistor 22 is felt and represents a logic high signal to be sent to control unit 5 (FIG. 1) which can be used by any associated circuitry. For example, control unit 5 may be an output microprocessor, such that the resulting output signal from output circuit 4 may be transmitted to the out microprocessor, which can contain logic to perform the turn on-off functions of the sump pump, sound an alarm, etc.

When the sensor pad area 31 is removed from the fluid, the charge across capacitor 12 equalizes, and transistor 13 becomes inactive. Therefore, oscillations cease.

The resistance R1 of resistor 16 determines how much of a difference in potential between pad 31 and the fluid is required before the oscillations in the oscillator circuit 2 begin. Therefore, the value of R1 determines what fluid will be detected by the pad. Table I shows various values of R1 and the fluids to which they correspond.

TABLE I

| R1 (kOhms) | Material |
| --- | --- |
| 1.0 | Nothing |
| 2.8 | Aviation Fuel |
| 3.08 | Water |
| 4.3 | Kerosene |
| 5.2 | Cooking oil |
| 6.2 | 40 Weight Oil |
| 10.0 | Air |

At a particular value of R1, only detection of that particular material will be accomplished; the presence of any other material is ignored. Furthermore, it has been determined through experimentation that slight changes in the value of R1 can enable detection of different fluids. As can be seen from this chart, as the value of R1 increases, the probe can detect heavier and heavier hydrocarbon molecules while ignoring everything else.

Referring again to FIG. 4, if the detection device of the present invention is intended for broad application, meaning that it is contemplated that the device would detect a number of different fluids, a potentiometer 100 (variable resistor) may substitute for resistor 16, and it may be communicate with oscillator circuit 2 via leads 102 connected to resistor terminals 103. Thus, various values of R1 can be used in the detection device, using a single probe, to adjust for detection of different types of fluids.

Alternatively, because the value of R1 determines what fluid is detected, the detector of the present invention can be constructed to identify an unknown fluid. Instead of using either resistor 16 or potentiometer 100, another microprocessor 105 can interface with circuit 50, such as by being connected to terminals 103 via leads 106. Once the probe is immersed into a fluid, microprocessor 105 is activated to automatically and continuously substitute a plurality of different values for R1 until oscillation conditions occur at a particular value of R1, at which time microprocessor 105 actuates an indicator identifying a fluid into which the probe is immersed. Such an indicator may be a series of lights, each light configured to be lit responsive to a corresponding R1 reading at the time of oscillation conditions. A panel housing the lights could bear indicia setting forth the name of the fluid corresponding to each R1 value. This embodiment of the present invention may therefore quickly identify an unknown fluid.

It is important to note, however, that the varying of R1 is not the only way to detect different fluids or to achieve broad application or fluid identification. For instance, the "Q-value" of inductor 15 can be changed to achieve the same results.

STRUCTURE OF A MODIFIED EMBODIMENT

A modified embodiment of the present invention differs from the preferred embodiment in two respects: (1) the pad area of the probe is bare, being neither encased in a potting material nor enclosed within a PVC shell, and (2) an additional capacitor is interposed intermediate the probe and the oscillator circuit.

First, as previously stated with regard to FIG. 2, pad area 31 is constructed of a metallic conductive material. A preferable material for a bare pad area is 316L stainless steel. Thus, the pad 31 of this embodiment directly contacts the fluid into which it is immersed.

Figure 5:
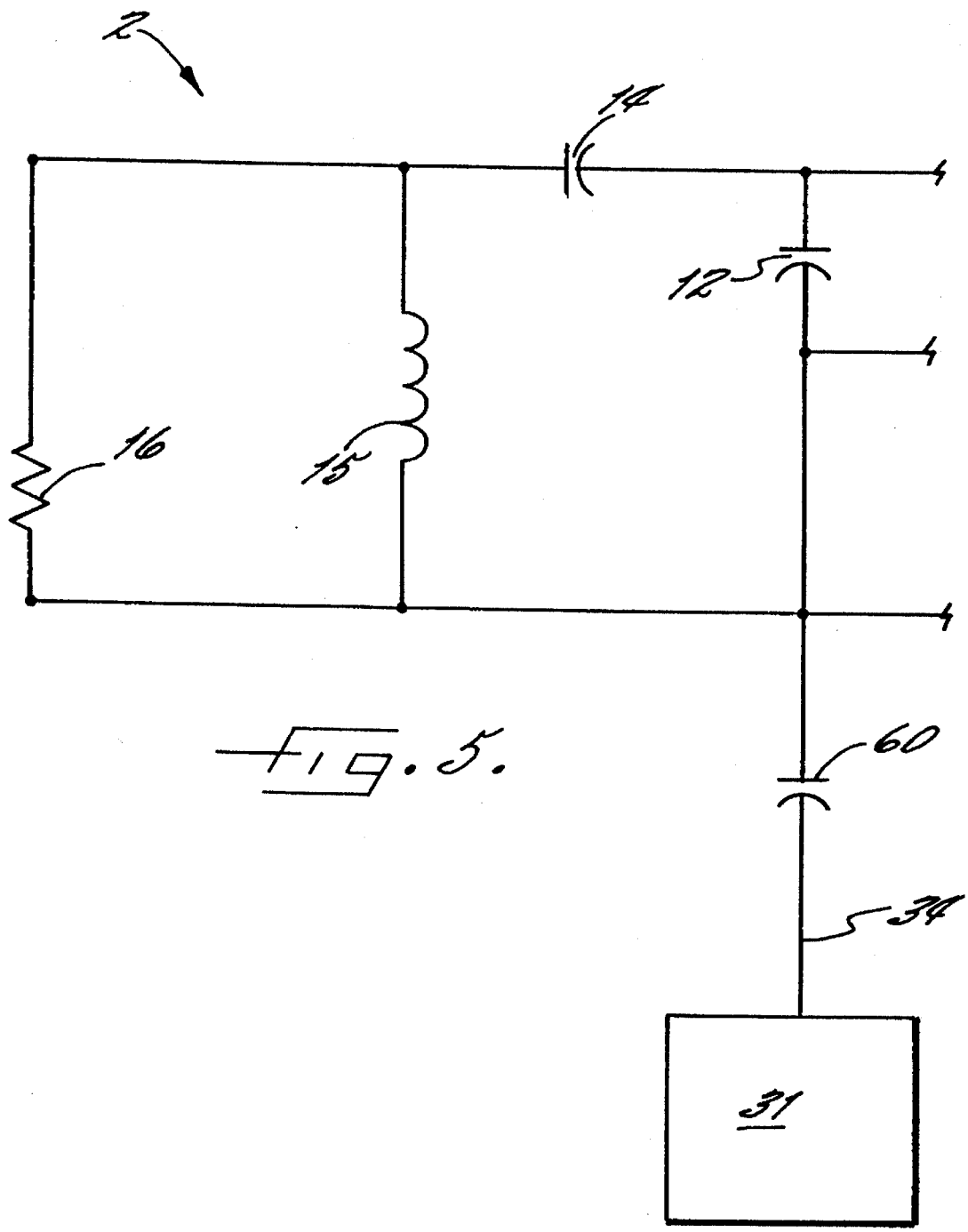
FIG. 5 is a schematic diagram of a portion of a circuit used in a modified embodiment of the present invention.

Second, referring to FIG. 5, a third capacitor 60 is interposed in the output 34 connecting the pad 31 and the oscillator circuit 2. The remainder of the circuit is identical to circuit 50, described with regard to the preferred embodiment. Third capacitor 60 removes DC potential that would otherwise be applied to pad 31, thereby preventing electrolysis of the fluid into which pad 31 is immersed. Despite the fact that the pad 31 in this embodiment is not charged, a field effect is still generated between it and the fluid due to the molecular structure of the stainless steel or other metal comprising the pad 31. If oscillation conditions are present, this field effect causes oscillation in the same manner as described with regard to the preferred embodiment.

OPERATION OF THE EMBODIMENTS

The structures of the respective embodiments of the invention having been described, operation of a detector constructed in accordance with either embodiment will now be described.

A particular use foreseen for the detecting device according to the invention is determining whether water has been mixed with oil. For this particular use, the value of R1 would be set to 3.08 kOhms and the probe 1 placed to the appropriate depth in the fluid source in accordance with the $S_f$ of the pad area. When no water is present, the pad 31 detects nothing and no oscillation occurs. This is because at this value of R1, the probe ignores everything but water. However, as soon as water is detected, the potential between it and the pad 31 will cause oscillation of current within the oscillator circuit 2. Then, the signal will be sent through the rest of the circuit and to the output circuit 4 of the detector. This output signal can activate an LED light, such as at 41 (FIG. 1) to detect the presence of water. If a microprocessor 5 is connected to the output circuit 4, the output signal can additionally cause the activation of an alarm 7. Such an arrangement may be employed to detect water in aviation fuel tanks or other tanks where the presence of water is not desirable.

The arrangement described immediately above could also be used in connection with concrete preparation, i.e., the detecting device can indicate when a concrete mixture has been cured. A probe, which would be used one time only, is inserted into a fresh concrete mixture. The field effect between the probe and the water in the mixture would be felt through the other concrete ingredients. In a sample construction according to this arrangement, an LED light may be activated until the portland cement in the concrete has been completely hydrated, at which time there would be no free water particles in the concrete left to cause the field effect.

As shown in FIG. 1, the detection device of the present invention can employ more than one sensor arrangement. Where two sensor arrangements are used, two types of fluids, such as oil v. water, can be distinguished, resulting in activation and deactivation of external devices. In such an instance, two sensors are employed, the sensor arrangements being identified as Types A and B, each sensor arrangement having oscillator circuit resistors of different resistances. Here, the first sensor (Type A) is set to detect oil only, while the second sensor (Type B) is set to detect water only. Both sensors are placed in the fluid, and as each detect their respective fluids, a microprocessor 5 can be used to determine the relative amounts of each.

The above dual sensor arrangement would be useful for determining the percentage of water emulsion in oils and for detecting oil spills at sea when placed on buoys. The greater the degree of refinement of oil, the easier it is for the Type A sensor to detect. Specifically, preparatory to an oil refinement process, positively charged plates are immersed into the crude oil to attract the negatively charged particles, i.e., water particles, thereto, thereby extracting them from the oil. Therefore, the greater the amount of refinement, the easier it is to detect the oil, e.g., aviation fuel is more refined than 40 weight oil.

The above dual sensor arrangement may also cause activation and deactivation of a sump pump, a function having particular application for natural oil storage tanks. Since extracted natural oil frequently contains ground water, the storage tank often contains a stratum of oil separated from and superposed upon a stratum of water. The detection device of the present invention can be lowered/installed into the oil storage tank both to determine the presence of water levels and to cause activation of a pump to remove the water only. When the Type B sensor detects water, its associated circuit is activated to cause activation of the sump pump to evacuate the water from the tank. When such evacuation is complete, the Type A sensor would detect the oil and send a signal to deactivate the sump pump. This would prevent the loss of oil being pumped with the water. A device constructed according to this arrangement could also be used in ship bilges and in processing tanks for cooking oils.

A multiple sensor arrangement could be used for detecting ground water contaminants. Such an arrangement contemplates a Type B sensor and a multiplicity of Type A sensors, each Type A sensor being set to detect different types of contaminants.

The above description is given in reference to a detection device. However, it is understood that many variations are apparent to one of ordinary skill in the art from a reading of the above specification and such variations are within the spirit and scope of the instant invention as defined by the following appended claims.

That which is claimed:

1. A detecting device for detecting a fluid, comprising:

a probe for detecting an electrical potential between itself and said fluid;

an output circuit in said probe, said output circuit producing an output signal when said electrical potential reaches a predetermined value;

a printed circuit board, said printed circuit board comprising a sensor pad area and a circuit area;

said sensor pad area being responsive to a difference in potential between itself and said fluid;

said sensor pad area sending a signal to said circuit area when said electrical potential reaches said predetermined amount;

a potting material encapsulating said printed circuit board; and an additive added to said potting material.

2. The detecting device according to claim 1 wherein said additive is graphite.

3. The detecting device according to claim 1 wherein said additive is powdered silver.

4. The detecting device according to claim 1 wherein a ratio of said additive to said potting material ranges from 0.5 grams/ounce to 1.0 grams/ounce.

5. The detecting device according to claim 1 further comprising an oscillator circuit in said probe, said oscillator circuit having predetermined component values dictating which particular type of fluid is detectable by said device.

6. The detecting device according to claim 5, wherein said oscillator circuit includes a potentiometer, whereby said device is adjusted to detect different types of fluids.

7. The detecting device according to claim 5, wherein said oscillator circuit includes a microprocessor, whereby said device is used to detect unknown fluids.

8. The detecting device according to claim 5, wherein said oscillator circuit comprises:

a pad area;

a first capacitor connected in series to said pad area;

an inductor connected in series to said capacitor; and a resistor connected in parallel to said inductor.

9. The detecting device according to claim 8, wherein resistance of said resistor determines which particular type of fluid is detectable by said device.

10. The detecting device according to claim 8, wherein a Q-value of said inductor determines which particular type of fluid is detectable by said device.

11. The detecting device according to claim 8, wherein said oscillator circuit further includes a second capacitor intermediate said pad area and said first capacitor.

12. The detecting device according to claim 8, further comprising:

an output line connecting said pad area to said oscillator circuit; and a third capacitor in said output line;

whereby a bare pad area directly contacts said fluid without occurrence of electrolysis.

13. The detecting device according to claim 11, further comprising a shell enclosing said printed circuit board, said shell being comprised of an inert and non-conductive material.

14. The detecting device according to claim 11, further comprising a transistor interfacing with said oscillator circuit, said transistor emitting an alternating current signal responsive to a change in voltage across said second capacitor.

15. The detecting device according to claim 14, further comprising a detector circuit communicating with said transistor, said detector circuit modifying said alternating current signal.

16. The detecting device according to claim 15, further comprising an amplifier circuit communicating with said detector circuit, said amplifier circuit amplifying a modified signal from said detector circuit and transmitting an amplified modified signal to said output circuit.

17. The detecting device according to claim 1, further comprising a light-emitting diode communicating with said output circuit, said light-emitting diode being activated responsive to said output signal.

18. The detecting device according to claim 1, further comprising:

a control unit interfacing said output circuit; and an external device activated or deactivated responsive to said output signal as transmitted by said control unit.

19. The detecting device according to claim 18 wherein said external device is a sump pump.

20. The detecting device according to claim 18 wherein said external device is an alarm.

* * * * *